United States Patent [19]

Lecolier et al.

[11] 4,242,280
[45] Dec. 30, 1980

[54] PROCESS FOR THE PREPARATION OF HALOGENO-MERCURI-ALDEHYDES AND -KETONES

[75] Inventors: Serge L. Lecolier, Janville sur Juine; Thierry A. Malfroot, Saint Germain les Corbeil; Marc D. Piteau, Itteville; Jean-Pierre G. Senet, Melun, all of France

[73] Assignee: Societe Nationale des Poudres et Explosifs, Paris, France

[21] Appl. No.: 968,281

[22] Filed: Dec. 11, 1978

[30] Foreign Application Priority Data

Dec. 23, 1977 [FR] France .................................. 77 39004

[51] Int. Cl.$^3$ ........................ C07C 47/14; C07C 47/52
[52] U.S. Cl. .................................................... 260/431
[58] Field of Search .......... 260/601 R, 593 H, 601 H, 260/590 R, 599, 590 C

[56] References Cited

PUBLICATIONS

Nesemeyonov, Chem. Abst., vol. 44, p. 7225.
Lutsenko et al., Chem. Abs., vol. 50, p. 4773b.
Nesemeyanov, Chem. Abs., vol. 50, p. 13730.
Nesemeyonov, Chem. Abs., vol. 52, p. 4476b.
Nesemeyonov, Chem. Abs., vol. 42, p. 4149a.

*Primary Examiner*—Werren B. Lone
*Attorney, Agent, or Firm*—Bucknam and Archer

[57] ABSTRACT

The invention relates to a process for the preparation of halogeno-mercuri-aldehydes and -ketones.

According to the invention, an alkenyl ester is reacted with a mercuric halide in the presence of water and, preferably, of an acid acceptor. The reaction, which is preferably carried out at between 15° and 35° C., makes it possible to obtain very pure products with excellent yields, especially when mercuric oxide is used as the acid acceptor.

13 Claims, No Drawings

PROCESS FOR THE PREPARATION OF HALOGENO-MERCURI-ALDEHYDES AND -KETONES

The present invention relates to a process for the preparation of halogeno-mercuri-aldehydes and -ketones.

In 1954, in the Bulletin de l'Academie des Sciences de l'URSS, Division Sciences Chimiques, pages 873–877, NESMEYANOV and PEREVALOVA showed the value of halogeno-mercuri-acetaldehydes, and especially chloro-mercuri-acetaldehyde, in the synthesis of numerous vinyl esters by reacting them with acyl chlorides.

The Applicant Company has also shown, in her French Patent Application 77/05,641, that it is possible to manufacture vinyl chloroformate from chloro-mercuri-acetaldehyde under excellent conditions. Taking account of the very great value of vinyl chloroformate and, to a lesser extent, of vinyl esters, chloro-mercuri-acetaldehyde is in great demand.

NESMEYANOV et al. initially proposed, op. cit. 1947, pages 63–69 (Chemical Abstracts 42, 4149a), to react butyl vinyl ether with mercuric acetate in the presence of water and then to add potassium chloride. LUTSENKO et al. subsequently recommended, in the same journal, pages 173–177 (1956) (Chemical Abstracts 50, 13730 g), to use an anhydrous ether medium and to hydrolyse the intermediate thus obtained. Finally, NESMEYANOV et al. used the same reactants together with mercuric oxide, in an alcoholic medium, and also produced the chloromercuric compound with an excellent yield (Izvest. Akad. Nauk. SSSR Otdel. Khim. Nauk., pages 942–948, 1957) (Chemical Abstracts 52, 4476b).

However, these processes are not satisfactory in terms of production on an industrial scale because they employ vinyl ethers which are expensive and because, in two cases, they employ reaction media which are relatively inconvenient to use.

Admittedly, NESMEYANOV et al. also proposed, in Izvest. Akad. Nauk. SSSR (1949), pages 601–606 (Chemical Abstracts 44, 7225c), to react alkenyl and mercury acetates in water, whilst stirring, to filter the mixture obtained and to add potassium chloride to the solution in order to finally obtain the chloro-mercuri-aldehyde or the chloro-mercuri-ketone. However, although it represents an improvement in terms of the costs relative to the processes referred to above, this process is not totally satisfactory because it proceeds in two stages and leads to products of mediocre purity which may be recrystallised in order to be suitable for storage without undergoing degradation.

Finally, in accordance with another method, it is possible to obtain a halogeno-mercuri-aldehyde by reacting a mercuric halide with mercuri-diacetaldehyde, as shown by LUTSENKO and KHOMUTOV in Doklad. Akad. Nauk. SSSR, 102, 97–99 (1955) (Chemical Abstracts 50, 4773b).

However, once again, this process is not very valuable because, on the one hand, mercuri-diacetaldehyde can already be used directly for synthesising vinyl chloroformate, and, on the other hand, the same expensive vinyl esters referred to above are required for the synthesis of the mercuri-diacetaldehyde itself.

A process for the manufacture of halogeno-mercuri-aldehydes and -ketones has now been discovered which makes it possible to manufacture these compounds in a single stage and from inexpensive raw materials.

The process according to the invention is characterised in that an alkenyl ester of a carboxylic acid is reacted with a mercuric halide in the presence of water.

According to a preferred embodiment of the invention, the reaction is carried out in the presence of an acceptor for the hydrogen halide acid which is formed.

In fact, it has been discovered that, surprisingly, alkenyl esters are sufficiently reactive towards mercuric halides to give rise to the reaction represented by the equation:

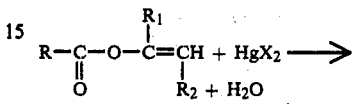

(I)

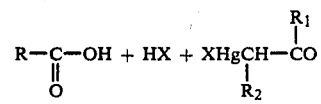

(II)

The halogeno-mercuri-aldehydes and -ketones to which the process according to the present invention relates are those of the general formula:

in which $X = Cl$ or $Br$, $R_1$ is a hydrogen or an alkyl group containing from 1 to 4 carbon atoms and $R_2$ is a hydrogen or alternatively forms, together with $R_1$, a cycloalkyl group containing from 5 to 7 carbon atoms.

The alkenyl esters of the formula (I) which can especially be used within the scope of the present invention are those in which $R_1$ and $R_2$ have the abovementioned meanings and in which R is an aliphatic group containing from 1 to 12 carbon atoms, which is optionally substituted by one or more identical alkenyloxycarbonyl groups, or alternatively R is an aromatic group. In other words, the preferred esters are alkenyl esters of aliphatic monoacids and polyacids and of aromatic monoacids.

In general terms, an ester such as those of short-chain alkanoic acids which are inexpensive, such as formates or acetates, is preferably used within the scope of the present invention.

The mercuric halides used according to the invention are mercuric chloride and bromide. The concentration of mercuric halide in the medium is such that it is either totally dissolved in the reaction medium or, preferably, partly dissolved and partly suspended in the said medium.

In the latter case, during the reaction and as the halogeno-mercuri-aldehyde or -ketone is formed, the proportion of mercuric halide in the suspension preferably decreases until it disappears, so that only the halogeno-mercuri-aldehyde or -ketone can easily be recovered, in the pure state, by filtration at the end of the reaction.

The reaction medium comprises either water on its own or a mixture of water and a water-miscible or -immiscible organic solvent. At least that amount of water which corresponds to the stoichiometry of the reaction (I) should be used in each case, but a large excess thereof is preferably employed.

In general terms, the reaction medium must be capable of solubilising, at least partially, the mercuric halide, the optional acid acceptor and, to a lesser extent, the alkenyl ester, at the reaction temperature.

Furthermore, those reaction media in which the halogeno-mercuri-aldehyde or -ketone is insoluble are particularly preferred. Thus, in the simplest version, which is not the least satisfactory, it is possible to use water on its own or water mixed with an amount (ranging from a small amount to a preponderant amount) of a water-miscible or -immiscible organic solvent such as acetone, methanol, ethanol, propanol, acetonitrile, nitrobenzene or toluene.

The suitable relative proportions of the various constituents are, in principle, the stoichiometric proportions but, in practice, it is very advantageous to use, on the one hand, as has been stated, a large excess of water relative to the other two reactants, and, on the other hand, a molar excess of alkenyl ester, preferably of 0 to 30%, relative to the mercuric halide. These conditions favour the rate and yield of the reaction and also the separation of the final product.

As has been stated above, according to a preferred variant of the invention, an acid acceptor is additionally used. Inorganic or organic acceptors, which are insoluble or partially or totally soluble in the reaction medium, can be used. Very suitable acid acceptors which may be mentioned are alkali metal or alkaline earth metal salts of organic acids or of weak inorganic acids, such as sodium carbonate, potassium carbonate or calcium carbonate, or sodium acetate or potassium acetate, alkali metal or alkaline earth metal hydroxides, such as sodium hydroxide, potassium hydroxide or slaked lime, or basic inorganic oxides such as quicklime or mercuric oxide. Whether or not it modifies the pH immediately, the acid acceptor can be introduced either all at once or in portions or also continuously throughout the reaction. If the acceptor does not modify the pH of the medium before the appearance of the hydrogen halide acid and the organic acid which form in accordance with the equation (I), it is advantageously introduced all at once, before the start of the reaction. This is the case, for example, of calcium carbonate which is insoluble in the medium in the absence of acids. If the acid acceptor immediately modifies the pH of the medium as soon as it is introduced, this being the case of the acceptors which are partially or totally soluble in water, it is also advantageous to introduce it as the reaction proceeds, in such a way that the pH of the reaction medium remains at an approximately constant value. This can be conveniently achieved by using, for example, an aqueous solution of sodium hydroxide or of potassium hydroxide.

However, it has been discovered that inorganic acceptors are slightly preferable to organic acid acceptors such as alkali metal salts of carboxylic acids. In fact, it has been found that the yield rarely exceeds 80% when halide ions and, to a lesser extent, carboxylates, are present in excess in the medium.

According to a particularly preferred variant of the process according to the invention, mercuric oxide is used as the acid acceptor. In fact, it has been discovered that despite its modest basic strength, the use of this substance is particularly advantageous for obtaining a final product of high purity and in a virtually quantitative yield, relative to the total mercury employed.

If mercuric oxide or any other acid acceptor is employed, one mol of acid acceptor should be used per n mols of mercuric halide, n being the number of basic sites on the said acceptor (for example n=1 in the case of sodium hydroxide and n=2 in the case of lime). When the acid acceptor is introduced, especially in the form of a single initial batch, the mercuric halide may be precipitated as mercuric oxide. It has been found that, contrary to expectation, this does not alter the reaction to any great degree and the reaction nevertheless takes place insofar as the pH of the reaction medium does not, however, exceed the value 12 and, preferably, the value 10.

As has been stated, the pH can be kept at an essentially fixed value during the reaction or, alternatively, it can be allowed to change freely. In the latter case, the pH of the reaction medium gradually decreases to reach a final value of the order of 2. In general, whether or not the pH is kept at a fixed value only has a slight influence on the course of the reaction. However, if it is desired to use an alkali metal salt of a carboxylic acid as the acid acceptor, it is necessary to keep the medium at an acid pH, which is preferably between 5 and 6, and to use a slight deficiency of the said salt relative to the mercuric halide, of the order of 10 mol %; otherwise, the yield is not optimum.

The reaction can be carried out at ambient temperature and this is particularly advantageous. However, it is possible to carry out the reaction at a different temperature, but this is preferably not greater than 60° C. (at which temperature there is in particular, decomposition in the medium of the product formed) and not less than $-10°$ C. The temperature, which is preferably between 15° and 35° C., can vary during the reaction; however, it is preferably kept constant and this can be achieved by varying the rate of introduction of the alkenyl ester, since the reaction is exothermic, or by cooling in a known manner.

As has been stated above, the reaction results from the action of an alkenyl ester on a mercuric halide. The alkenyl ester is preferably introduced into the solution or solution/suspension of mercuric halide in the reaction medium which optionally comprises an acid acceptor. When all the alkenyl ester has been introduced, the reaction is virtually complete. However, once the alkenyl ester has been introduced, the reaction is preferably allowed to continue, whilst stirring the mixture and preferably keeping the temperature at the level at which the introduction was carried out. At the end of this period, the duration of which is preferably from 20 to 60 minutes, the heterogeneous mixture obtained is filtered and the halogenomercuri-aldehyde or -ketone is collected in the form of crystals, directly in the very pure state. If desired, the products obtained can be recrystallised from water.

The yield of the reaction depends, in particular, on the nature of the reaction medium used and the presence and nature of the acid acceptor. In general terms, the yield is higher in pure water than in homogeneous or heterogeneous mixtures of water with other solvents. Likewise, the yield rarely exceeds 20% in the absence of an acid acceptor. On the other hand, the yield is generally between 70 and 90% when using an alkali metal salt of a carboxylic acid or, preferably, inorganic bases such as water-soluble or -insoluble carbonates, alkali metal or alkaline earth metal hydroxides or basic oxides.

In the case of mercuric oxide, the yield is particularly good, namely between 95 and 100%, when using about one mol of mercuric oxide and two mols of alkenyl ester per mol of mercuric halide.

The purity of the products obtained generally improves as the yield produced by the acid acceptor used increases. By virtue of the process according to the invention, it is possible to achieve, without recrystallisation, degrees of purity which have never been achieved hitherto. However, this purity is influenced by the moisture content of the product. In the case of prolonged storage, it is advisable to dry the halogeno-mercuri-aldehydes and -ketones thoroughly, for example by azeotropic distillation with methylene chloride.

The value of the process according to the invention will be particularly appreciated, not only in terms of the excellent yields and degrees of purity which can thereby be achieved, but also in terms of the production costs. In fact, alkenyl esters, and in particular vinyl acetate, are very inexpensive raw materials and mercuric halides are generally less expensive than the other mercury salts; in particular, mercuric chloride is more accessible than the acetate. Furthermore, from the point of view of the production of vinyl or isopropenyl chloroformate or vinyl esters, it is of the greatest value to be able to re-use all the mercuric chloride which is obtained for each mol of these derivatives formed, all the more so because mercuric oxide is easily obtained, for example by the action of an alkali metal hydroxide on the said mercuric chloride.

Thus, the process according to the invention, which can be carried out discontinuously or continuously, is admirably suited to integration in a plant for the production of the abovementioned industrial products, in which the mercuric salts circulate in a closed circuit, thus removing the dangers of mercury pollution.

The following examples are given by way of nonlimiting illustrations of a few variants of the process according to the invention. Other variants, especially those based, for example, on the availability of raw materials which are unusual but obtainable as by-products of other industrial manufacturing processes, can easily be designed by those skilled in the art.

EXAMPLE 1

135 g of mercuric chloride, that is to say 0.5 mol, and 36.9 g of sodium acetate, that is to say 0.45 mol, as the acid acceptor, were introduced into a 500 ml reactor equipped with a mechanical stirrer, a thermomemter and a condenser.

56 g of vinyl acetate, that is to say 0.65 mol, were run dropwise into the medium obtained, whilst keeping the temperature below 30° C.

Once the addition was complete, the medium obtained was stirred for one hour at ambient temperature. The solid obtained was then isolated by filtration and washed with ethyl ether.

A total of 109 g of chloro-mercuri-acetaldehyde, melting at 130° C., was collected.

The yield is 78%, relative to the mercuric chloride.

EXAMPLE 2

The reaction was carried out under the same conditions as in Example 1, but without using sodium acetate or any other acid acceptor.

In this case, only 28 g of chloro-mercuri-acetaldehyde, melting at 130° C., are formed, that is to say a yield of only 20%.

EXAMPLE 3

67.9 g (0.25 mol) of mercuric chloride, 200 ml of water and 18.5 g (0.225 mol) of sodium acetate were introduced into a 500 ml reactor. 28 g of vinyl acetate were run, in the course of 20 minutes, into the medium obtained, whilst keeping the temperature at 40° C. and stirring the medium with a stirrer of the rotating anchor type.

After one hour, the salt, suspended in ether, was filtered off and dried in vacuo over $P_2O_5$. This gave 41.9 g of chloro-mercuri-acetaldehyde, melting at 130° C., that is to say a yield of 60%.

EXAMPLE 4

All the conditions of the preceding example were repeated, except that the temperature was kept at 60° C.

This gave only 36.9 g of chloro-mercuri-acetaldehyde, melting at 124° C., that is to say a yield of 52.8%.

EXAMPLE 5

The conditions of the preceding Examples 3 and 4 were repeated, except that the temperature was kept at 22° C., and they were applied to four-fold amounts of reactants. Chloro-mercuri-acetaldehyde, melting at 130° C., was obtained with a yield of 76%.

EXAMPLE 6

600 ml of water and 203.7 g (0.75 mol) of mercuric chloride were introduced into a 2 liter reactor.

64.5 g of vinyl acetate were then introduced and, as soon as the pH had reached the value 3, it was kept at this value by adding 3 N sodium hydroxide solution.

By keeping the temperature at 22° C. and prolonging the reaction by one hour after the addition, 157 g of chloro-mercuri-acetaldehyde were finally obtained, that is to say a yield of 75%.

The product obtained melted at 132° C.

EXAMPLE 7

The same initial proportions were used as in the preceding Example 6, but, this time, 1 N sodium hydroxide solution was used to effect the same pH variation in the medium as was observed naturally in Example 5, and sodium acetate was used as the acid acceptor.

The pH thus changed between the values 6.4 (initially) and 2 (at the end). The temperature was kept constant at 22° C.

This gave 150.2 g of chloro-mercuri-acetaldehyde, melting at 131° C., that is to say a yield of 71.8%.

EXAMPLE 8

The same conditions as in Example 6 were repeated, but 3 N sodium hydroxide solution was used to keep the pH of the reaction medium between 6 and 6.5 throughout the addition of the vinyl acetate. The temperature was fixed at 22° C.

Chloro-mercuri-acetaldehyde, melting at 127°–128° C., was finally obtained with a yield of 89.5%.

EXAMPLE 9

The experiment of Example 7 was re-started, using sodium carbonate as the acid acceptor.

The reaction was carried out at 22° C. and the pH changed between the values 6.2 and 2.5.

This gave 145.4 g of chloro-mercuri-acetaldehyde, melting at 133° C., that is to say a yield of 69.5%.

The evolution of carbon dioxide gas and the consequent formation of a fairly copious foam were observed during the reaction.

EXAMPLE 10

A mixture of 50 ml of water and 150 ml of ethanol and the amounts of reactants of Example 5 were used as the reaction medium.

This gave chloro-mercuri-acetaldehyde, melting at 130° C., with a yield of 70.6%.

EXAMPLE 11

The conditions of Examples 5 and 10 were repeated, but the water and the ethanol/water mixture, respectively, were replaced by a 50/50 mixture of water and methylene chloride.

This gave chloro-mercuri-acetaldehyde, melting at 134° C., but with a yield of only 35%.

EXAMPLE 12

A 50/50 mixture of water and nitrobenzene was used in this experiment. By keeping the temperature at 20° C. and the other operating conditions the same as those of Examples 10 and 11, chloro-mercuri-acetaldehyde, melting at 134° C., was obtained with yield of 42%.

EXAMPLE 13

The procedure of the preceding Examples 10 to 12 was followed using, this time, a 50/50 mixture of water and toluene, at 22° C.

This gave chloro-mercuri-acetaldehyde, melting at 120° C., with a yield of 58.5%.

EXAMPLE 14

The method of operation of Example 5 was repeated in every respect, but the reaction was stopped and the solid obtained filtered off as soon as the introduction of the vinyl acetate had ended or, in other words, the reaction was not completed by stirring the medium for one hour at 22° C.

This gave chloro-mercuri-acetaldehyde, melting at 130° C., with a yield of 61%.

EXAMPLE 15

180 g (0.5 mol) of mercuric bromide, 400 ml of water and 36.9 g of sodium acetate were placed in a one liter reactor.

The temperature of the medium was kept at between 18° and 24° C. and 56 g of vinyl acetate were run into the above solution/suspension, whilst stirring.

Once the introduction was complete, the reaction mixture was stirred for a further 30 minutes at ambient temperature, after which the white solid obtained was filtered off, washed with ether and dried in vacuo.

121.3 g of bromo-mercuri-acetaldehyde, identified by its NMR spectrum and melting at 120° C., were thus collected.

The yield is 75%, relative to the mercuric bromide.

EXAMPLE 16

67.9 g of $HgCl_2$ (0.25 mol), a batch of 12.5 g (0.125 mol) of powdered calcium carbonate (containing 0.25 mol of basic sites) and 200 ml of water were placed in a 500 ml reactor. The pH of this medium is about 7.

28 g (0.325 mol) of vinyl acetate were then introduced, whilst stirring and keeping the temperature at between 25° and 35° C. The mixture was stirred for one hour at 25° C. and, after filtration, washing and drying, extremely pure chloro-mercuri-acetaldehyde, melting at 134° C. (compared with 130° C. as indicated in the literature), was obtained with a yield of 82.5%.

EXAMPLE 17

The method of operation of Example 16 was repeated using calcium hydroxide (0.125 mol) in place of the calcium carbonate. The initial pH was equal to 9 and a precipitate of HgO was observed. This gave chloro-mercuri-acetaldehyde, melting at 133° C., with a yield of 77%.

EXAMPLE 18

The procedure of Examples 16 and 17 was repeated using, this time, an initial batch of 0.25 mol of sodium hydroxide.

The medium, in which a precipitate of mercuric oxide was observed, had an initial pH of 9.5.

This gave chloro-mercuri-acetaldehyde, melting at 134° C., with a yield of 75.5%.

The same experiment, carried out using ammonia, gives a 40% yield of chloro-mercuri-acetaldehyde which decomposes at between 124° and 130° C.

EXAMPLE 19

The method of operation of the preceding Examples 16 to 18 was used with 0.25 mol of $HgCl_2$, 0.65 mol of vinyl acetate, 0.25 mol of mercuric oxide and 200 ml of water.

The initial pH was between 4 and 5.

This gave 66.7 g of chloro-mercuri-acetaldehyde, melting at 134° C., that is to say a yield of 95.7%.

EXAMPLE 20

The operation of Example 19 was repeated.

This gave 67.4 g of very pure chloro-mercuri-acetaldehyde, melting at 134° C., that is to say a yield of 96.6%.

It should be noted that, in this experiment, as in the preceding experiment, the medium is initially red in colour (HgO) and that it has become white in colour by the end of the reaction, this being a convenient means of following the course of the reaction.

EXAMPLE 21

It was desired to demonstrate the adverse influence of the presence of an excess of chloride ion in the medium.

For this purpose, the operations of Examples 19 and 20 were repeated in the presence of 0.5 mol of potassium chloride.

In this case, with all other things being equal, only 46.9 g of chloro-mercuri-acetaldehyde, melting at only 130° C., were obtained, that is to say a yield of 67.3%.

EXAMPLE 22

54.15 g (0.25 mol) of mercuric oxide, 67.9 g (0.25 mol) of mercuric chloride and 200 ml of water were placed in a 500 ml reactor.

The temperature was kept at about 22° C. and 65 g of isopropenyl acetate were run in over a period of 15 minutes whilst stirring. Once the addition was complete, the medium was stirred for 45 minutes at ambient temperature. The white solid obtained was then isolated by filtration. After washing with ethyl ether and drying in vacuo, 61.2 g of chloro-mercuri-acetone, $ClHgCH_2COCH_3$, were obtained, that is to say a yield of 88.2%.

This compound melts at 106° C. (literature: 106° C.) and contained 0.39% by weight of water.

We claim:

1. A one step process for the synthesis of a halogeno-mercuri-aldehyde or -ketone, of formula $$XHgCH_2-COR_1$$

in which $R_1$ is H or methyl, X is Cl or Br which comprises reacting an alkenyl ester of a carboxylic acid with mercuric chloride or bromide in the presence of water, said alkenyl ester of said carboxylic acid having the formula $$R-\underset{\underset{O}{\|}}{C}-O-\underset{\underset{R_1}{|}}{C}=CH_2$$

in which $R_1$ is as defined hereinabove, R is H or an alkyl of 1 to 12 carbon atoms or phenyl, said reaction being carried out in the presence of an acid acceptor, at a temperature between $-10°$ C. and $+60°$ C. and isolating said halogeno-mercuri-aldehyde or ketone from the reaction mixture.

2. Process according to claim 1, wherein the acid acceptor is a member selected from the group consisting of alkali metal and alkaline earth metal salts of organic acids, alkali metal and alkaline earth metal salts of weak inorganic acids, alkali metal and alkaline earth metal hydroxides and basic inorganic oxides.

3. Process according to claim 2, wherein the acid acceptor is a member selected from the group consisting of sodium acetate, potassium acetate, calcium carbonate, sodium hydroxide, potassium hydroxide, calcium hydroxide and calcium oxide.

4. Process according to claim 2, wherein the acid acceptor is mercuric oxide.

5. Process according to claim 3, wherein about one mol of acid acceptor is used per n mols of mercuric halide, n being the number of basic sites on the said acceptor.

6. Process according to claim 5, wherein all the acceptor is introduced in the form of a single initial batch.

7. Process according to claim 1, wherein the reaction is carried out in the presence of a large excess of water, relative to the other reactants, and of a 0 to 30% excess of alkenyl ester, relative to the mercuric halide.

8. Process according to claim 4, wherein one mol of mercuric oxide and two mols of alkenyl ester are used per mol of mercuric halide.

9. Process according to claim 7, wherein water mixed with a water-miscible or -immiscible organic solvent is used.

10. Process according to claim 1 wherein the reaction is carried out at a temperature between 15° and 35° C.

11. Process according to claim 1 wherein the alkenyl ester is introduced into the solution or solution/suspension of mercuric halide in the reaction medium which optionally comprises an acid acceptor.

12. Process according to claim 11, wherein after the alkenyl ester has been introduced, the reaction is allowed to continue, whilst stirring the mixture.

13. Process according to claim 12, wherein the reaction is continued for 20 to 60 minutes.

* * * * *